(12) United States Patent
Lardi et al.

(10) Patent No.: US 9,804,063 B2
(45) Date of Patent: Oct. 31, 2017

(54) SAMPLING DEVICE FOR SAMPLES CONTAINING DNA IN PARTICULAR

(71) Applicant: PRIONICS AG, Schlieren (CH)

(72) Inventors: Eligio Lardi, Winterthur (CH); Christoph Stamm, Stein am Rhein (CH); Bernhard Hostettler, Gockhausen (CH); Mathias Blaser, Zürich (CH); Andreas Rüegg, Zürich (CH)

(73) Assignee: PRIONICS AG, Schlieren (CH)

( * ) Notice: Subject to any disclaimer, the term of this patent is extended or adjusted under 35 U.S.C. 154(b) by 163 days.

(21) Appl. No.: 14/420,026

(22) PCT Filed: Jul. 31, 2013

(86) PCT No.: PCT/EP2013/002264
§ 371 (c)(1),
(2) Date: Feb. 6, 2015

(87) PCT Pub. No.: WO2014/023399
PCT Pub. Date: Feb. 13, 2014

(65) Prior Publication Data
US 2015/0226646 A1 Aug. 13, 2015

(30) Foreign Application Priority Data

Aug. 7, 2012 (DE) .................... 10 2012 015 706

(51) Int. Cl.
*G01N 1/02* (2006.01)
*B01L 3/00* (2006.01)
(Continued)

(52) U.S. Cl.
CPC ........... *G01N 1/02* (2013.01); *A61B 10/0045* (2013.01); *A61F 13/38* (2013.01); *B01L 3/508* (2013.01);
(Continued)

(58) Field of Classification Search
CPC .... G01N 1/02; G01N 2001/028; B01L 3/508; B01L 2300/041; B01L 2200/04;
(Continued)

(56) References Cited

U.S. PATENT DOCUMENTS

| 6,514,224 B1 | 2/2003 | Anapliotis |
| 2005/0010132 A1 | 1/2005 | Pestes et al. |

(Continued)

FOREIGN PATENT DOCUMENTS

| DE | 19900683 A1 | 7/2000 |
| DE | 102005034217 A1 | 2/2007 |

(Continued)

OTHER PUBLICATIONS

English Translation of the International Preliminary Report on Patentability dated Feb. 10, 2015 in corresponding International Patent Application No. PCT/EP/2013/002264, filed Jul. 31, 2013.

*Primary Examiner* — Jill Warden
*Assistant Examiner* — Julie Tavares
(74) *Attorney, Agent, or Firm* — Peter G. Foiles; Gregory H. Kline

(57) ABSTRACT

Sampling device for samples containing DNA in particular, with a sample-collecting area provided at the free end of an elongate holding device, wherein the sample-collecting area is designed to be separable from the sampling device.

8 Claims, 5 Drawing Sheets

(51) Int. Cl.
  *A61B 10/00* (2006.01)
  *A61F 13/38* (2006.01)
  *A61B 10/02* (2006.01)
(52) U.S. Cl.
  CPC ... *A61B 2010/0216* (2013.01); *B01L 2200/04* (2013.01); *B01L 2300/041* (2013.01); *B01L 2300/0832* (2013.01); *G01N 2001/028* (2013.01)
(58) Field of Classification Search
  CPC ............. B01L 2300/0832; A61F 13/38; A61B 10/0045; A61B 2010/0216
  USPC ......... 422/405, 411, 500, 501, 547; 73/1.73, 73/1.74; 435/288.1
  See application file for complete search history.

(56) References Cited

U.S. PATENT DOCUMENTS

| | | |
|---|---|---|
| 2008/0077046 A1 | 3/2008 | Burg |
| 2009/0156962 A1* | 6/2009 | Yong .................. A61B 10/0045 600/569 |

FOREIGN PATENT DOCUMENTS

| | | |
|---|---|---|
| WO | 02/070644 A1 | 9/2002 |
| WO | 2007/009414 A1 | 1/2007 |

* cited by examiner

SAMPLING DEVICE FOR SAMPLES CONTAINING DNA IN PARTICULAR

The invention relates to a sampling device for samples containing DNA having a sample-collecting area provided at a free end of an elongate holding device, wherein the sample-collecting area is separable from the sampling device.

Devices according to the preamble are used particularly in the field of forensics but also in other fields, for example, medical applications. They are used for removing or securing sample material which is then analyzed in a downstream step in the laboratory.

Such devices suitable for sampling are also referred to as swab, dabber or also forensic sticks for professional use. They comprise an elongate, generally rod-shaped holding area, by means of which a sample-collecting area arranged at the distal end of the holding area can be moved during the sampling. The sample-collection area can be formed, for example, from a cotton wad. However, other materials are also conceivable, for example, flocked nonwoven fabrics. The only important factor is that the sample-collecting area is made of a material that is capable of lastingly accommodating the sample until the treatment in the laboratory and then of releasing it again in the course of the analysis for treatment with appropriate buffers, etc.

As already mentioned above, a substantial aspect of processing, forensic sample material, for example, is the analysis in the laboratory. Here genetic, immunological or other analyses can occur, for example.

As a general rule, for the investigation in the laboratory, the sample-collecting area is transferred into a vessel in which either only the extraction of the sample contained occurs, or, on the other hand, the further processing is also already carried out, in addition. These vessels can be, for example, so-called spin baskets, but also any other laboratory vessels provided for this purpose, such as Eppendorf caps, etc.

In the context of the downstream processing in the laboratory, the elongate holding device causes interference. Therefore, the sample-collecting area is commonly separated from the holding device before the processing. Here, one must carefully ensure that no contamination of the sample-collecting area occurs in the context of the separation. Moreover, in the context of laboratory logistics and also with a view to the number of samples to be processed, which is as a general rule relatively large, a largely automated procedure is desirable.

In this context, sampling devices are known, which have a sample-collecting area that is detachably connected to the holding device. In the case of a corresponding device known from EP 1409636, it is provided moreover for the vessel used for the processing in the laboratory to comprise devices in the interior that allow the introduction of the sample-collecting area into the vessel but that retain the sample-collecting area as the holding device is pulled out of the vessel. In the case of further movement of the holding device, the connection between it and the sample-collecting area is undone and the interfering holding device can be removed separately.

However, the known device has the disadvantage that, for the automated separation of the sample collecting area from the holding device, the sampling device does not only need to be produced appropriately. Rather, the above-mentioned devices that retain the sample-collecting area also have to be provided in the laboratory vessel provided for the processing.

Therefore, the problem of the invention is to produce a sampling device which allows the automated separation of sample-collecting area from holding device, without requiring special laboratory vessels for that purpose.

The problem is solved with a sampling device that comprises a sample-collecting area provided at a free end of an elongate holding device, wherein the sample-collecting area is separable from the sampling device, wherein the holding device, when viewed in a longitudinal direction, has a proximal segment with an inner recess extending from a distal end thereof at least over a longitudinal area in a proximal direction, and a sleeve that is aligned distally flush with respect to the recess, wherein the proximal segment and the distal sleeve are connected to one another by means of a plug that is inserted with little clearance in the inner recess and the sleeve, wherein the dimensions of the plug, of the sleeve and of the inner recess are adjusted to one another such that in normal operation a stable connection of the proximal segment to the sleeve is established, and wherein the sample-collecting area is arranged on an elongate extension whose free end is inserted in turn with little clearance in a distal end of the sleeve, wherein lengths of the inner recess, of the sleeve, of the plug and of the extension are adjusted to one another such that the plug can be completely inserted into the recess in the case of a proximally directed displacement of the extension relative to the sleeve, and, optionally, wherein the plug and/or extension is/are secured in the sleeve and/or inner recess by means of a positive-fit connection.

According to the invention, a first variant of the sampling device comprises an elongate holding device which, viewed in the longitudinal direction, is subdivided into a proximal segment and a distal sleeve. The proximal segment here has an inner recess extending over one from its distal end in the proximal direction or is preferably also formed as a continuous sleeve.

The distal sleeve is aligned distally flush with respect to the recess. Proximal segment and sleeve are connected to one another via a plug that can be inserted with little clearance both in the inner recess and also in the sleeve. The dimensions of the plug as well as of the inner recess and of the sleeve are here adjusted to one another such that, in normal operation of the device, a stable connection of the two segments is guaranteed. On the other hand, if a defined higher force is used, beyond what is usual in the sampling operation, it must be possible to displace the plug in the mentioned parts connected by said plug.

As for the sample-collecting area, it is arranged at the one end of an elongate extension whose other end is inserted into the distal end of the sleeve.

The sampling device according to the invention thus comprises a two-part holding device of which the two segments are connected to one another via the plug. The sample-collecting area is attached to the holding device at the distal end of the sleeve via an extension inserted in the sleeve there.

The dimensions of the inner recess, of the sleeve, of the plug and of the extension that holds the sample-collecting area are adjusted to one another in an embodiment so that, during normal operation of the sampling device, for example all or at least some parts are secured to one another with a tight fit.

An additional embodiment relates to securing by means of a positive-lock engagement. In this embodiment, it is provided that the plug and/or extension in the sleeve and/or inner recess are secured, for example, by means of a snap-in connection. For this purpose, the plug and/or extension present(s) outward pointing snap-in noses which engage, for example, under spring force, in inner recesses or perforations in the sleeve or inner recess. The snap-in noses are designed so that the snap-in engagement is released in the case of a proximal displacement of the extension, and an additional proximal displacement of extension and plug is possible.

Naturally, it is also conceivable to provide combinations of tight-fit securing and positive-lock securing in a sampling device.

It is essential for the invention that in the case of the application of a force that exceeds a defined value and acts, for example, in the longitudinal direction downward onto the proximal end of the sampling device in the case of an immobilized distal end, a displacement of the mentioned components is possible. In such a case, the proximal segment is displaced, together with the distal sleeve adjoining said proximal segment, relative to the extension and the plug. The plug in the process moves, pushed by the extension in the proximal direction, into the recess of the proximal segment and, if it has been pushed completely into this recess, it releases the connection between the proximal segment and the sleeve. The sample-collecting area is then separated together with the sleeve from the proximal segment of the sampling device.

It should be understood that the inner recess of the upper segment has to be formed so that it is sufficiently long to allow the plug to be pushed in completely.

With the device according to the invention, a particularly simple automated separation of the sample-collecting area is possible. It is sufficient to immobilize the device on the proximal end and to introduce it with the distal end that forms the sample-collecting area one into a vessel, until said area comes in contact with the bottom of the vessel. If the proximal end is then moved further in the direction of the bottom of the vessel, then the above-described relative displacement of extension and plug relative to the enclosing parts of the holding device occurs, with the result that the sample-collecting area is separated from the upper segment of the holding device.

It should be understood that the dimensioning of the segments can be selected as desired. With a view to the desired separation of substantially only the sample-collecting area, it is probable that in most applications the proximal segment will be formed so that it is clearly longer than the sleeve distally adjoining thereto.

In order to prevent an unintentional separation of the sample collecting area during the sampling, for example, by pushing too hard on it, it is possible, in an advantageous embodiment, to provide a limiting device which can be inserted in the upper segment and which blocks the recess. This limiting device can be removed in the laboratory, after which the above-described separation of the sample-collecting area can then be carried out.

If a holding device is used in which the upper segment as well is formed as a continuous sleeve, then it is also conceivable to form the plug provided for the connection of the two segments so that it is sufficiently long to reach the proximal end of the proximal segment, and to provide there, for example, a cap or the like which prevents the plug from being displaced in the proximal direction. It is only after the removal of the cap that the mentioned separation of the collecting area can occur in turn.

In additional variants of a sampling device according to the invention, it is possible to provide that the holding device has an inner rod-shaped device at the distal end of which the sample-collecting area is arranged detachably. Moreover, the holding device has an external device that encloses at least partially the inner rod-shaped device in the longitudinal and peripheral directions. The internal and external devices are adjusted relative to one another, wherein it is provided that, as a result of a defined relative movement of two devices, the sample-collecting area is separated from the holding device.

In an embodiment, the internal device is a small rod with two segments that are connected to one another via a predetermined breaking point. The external device is a small tube that partially encloses the small rod in longitudinal direction. Moreover, it is provided for that the small rod and the small tube are in engagement distally relative to the predetermined breaking point, in a manner which prevents twisting. If a rotation is then applied at the proximal end of the small tube, then, due to the distal protection against twisting between the small tube and the small rod, the predetermined breaking point is destroyed, and the portion of the small rod which extends distally away from said point and which carries the sample-collecting area is separated.

In a further embodiment, an inner small rod and a small tube partially enclosing the small rod are again provided. The small rod consists of two segments, a distal segment carrying the sample-collecting area and, arranged adjoiningly thereto, a proximal segment which projects upward. During operation, the separation site between the distal segment and the proximal segment of the small rod is surrounded by the outer small tube. In order to prevent the distal segment from falling out, a positive-locking engagement can be provided between said segment and the small tube.

For the separation, the proximal area of the small rod, which projects upward viewed relatively, is pressed into the enclosing small tube. It is conceivable that the small rod moves and that the small tube is stationary. However, it is equally possible for the small tube to be displaced upward relative to a stationary small rod. In both cases, the separation site between the distal and the proximal segment is moved downward out of the small tube, as a result of which the sample-collecting area together with the distal area of the small rod is separated from the holding device.

It is understood that the above-mentioned positive lock between the distal area of the small tube and the sleeve must be selected so that it can be undone without exerting excessive force when the small rod is pressed in.

Here, different conceivable possibilities as to how the distal segment of the small rod is received in the small tube are described in the following FIGS. (4, 5ab).

Finally, an additional variant provides that the holding device again comprises in particular an inner small rod as well as an external device arranged parallel to said inner small rod and at least partially surrounding the small rod. The external device and the small rod are inserted at their distal end with a tight fit into a recess which carries the sample-collecting area at its other end. If, as a result of relative movement between the internal and external devices, the external device is then pulled out of the extension, the attachment is undone again as a result, and the extension as well as the sample-collecting area are automatically separated.

Below, the invention will be explained in greater detail in reference to several figures.

Figure 3:
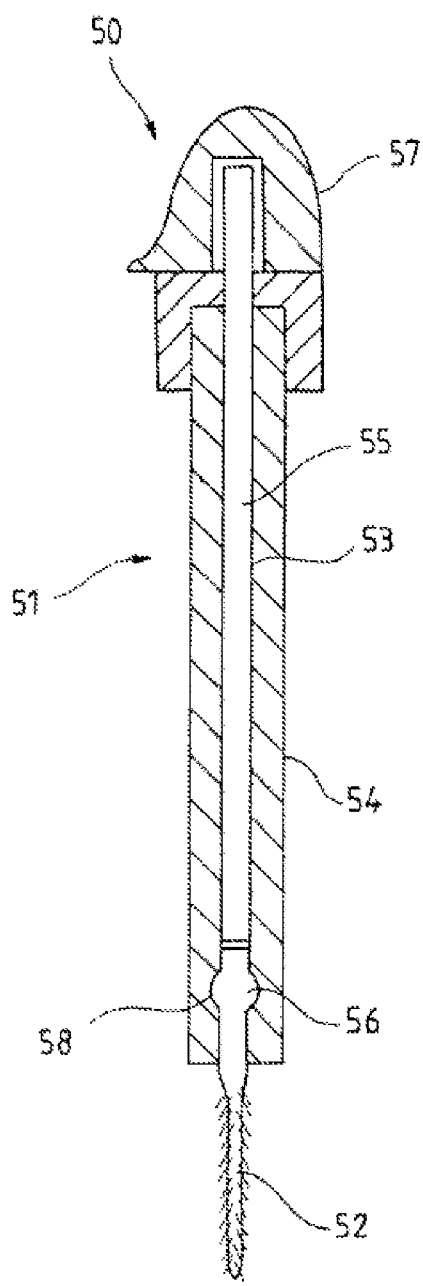
Figure 4:
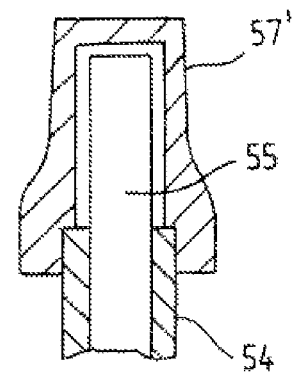
Figure 5A:
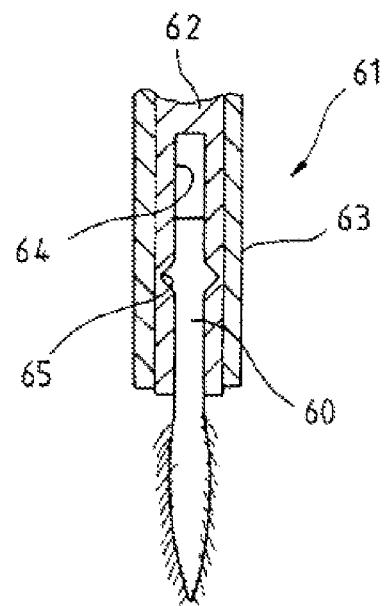
Figure 6:
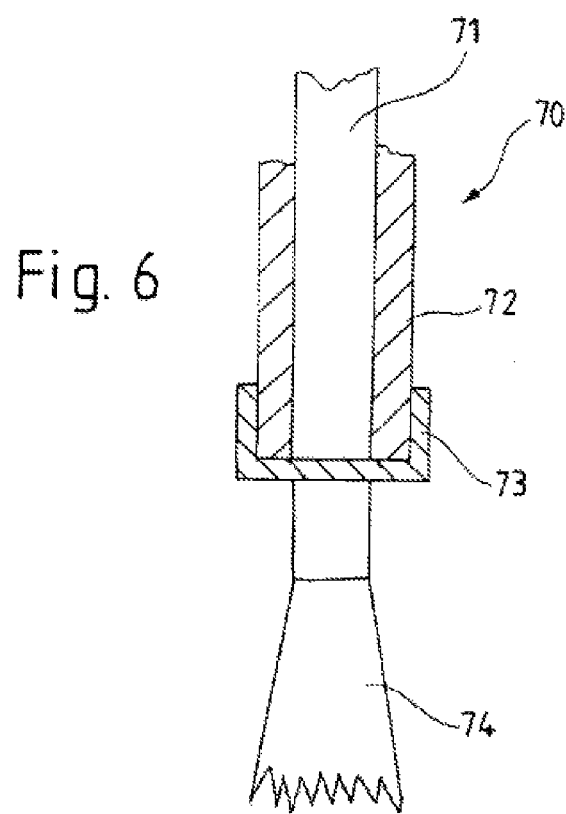

FIG. 3 shows a sampling device according to an additional variant, in which the separation of the sample-collecting area occurs by pushing an internal device forward relative to an external device of the holding device, FIG. 4 shows an alternative embodiment of the proximal end of the sampling device shown in FIG. 3, FIGS. 5a/5b show an alternative embodiment of the distal end of the sampling device shown in FIG. 3, and FIG. 6 shows an additional embodiment of a sampling device according to an additional variant.

Figure 1A:
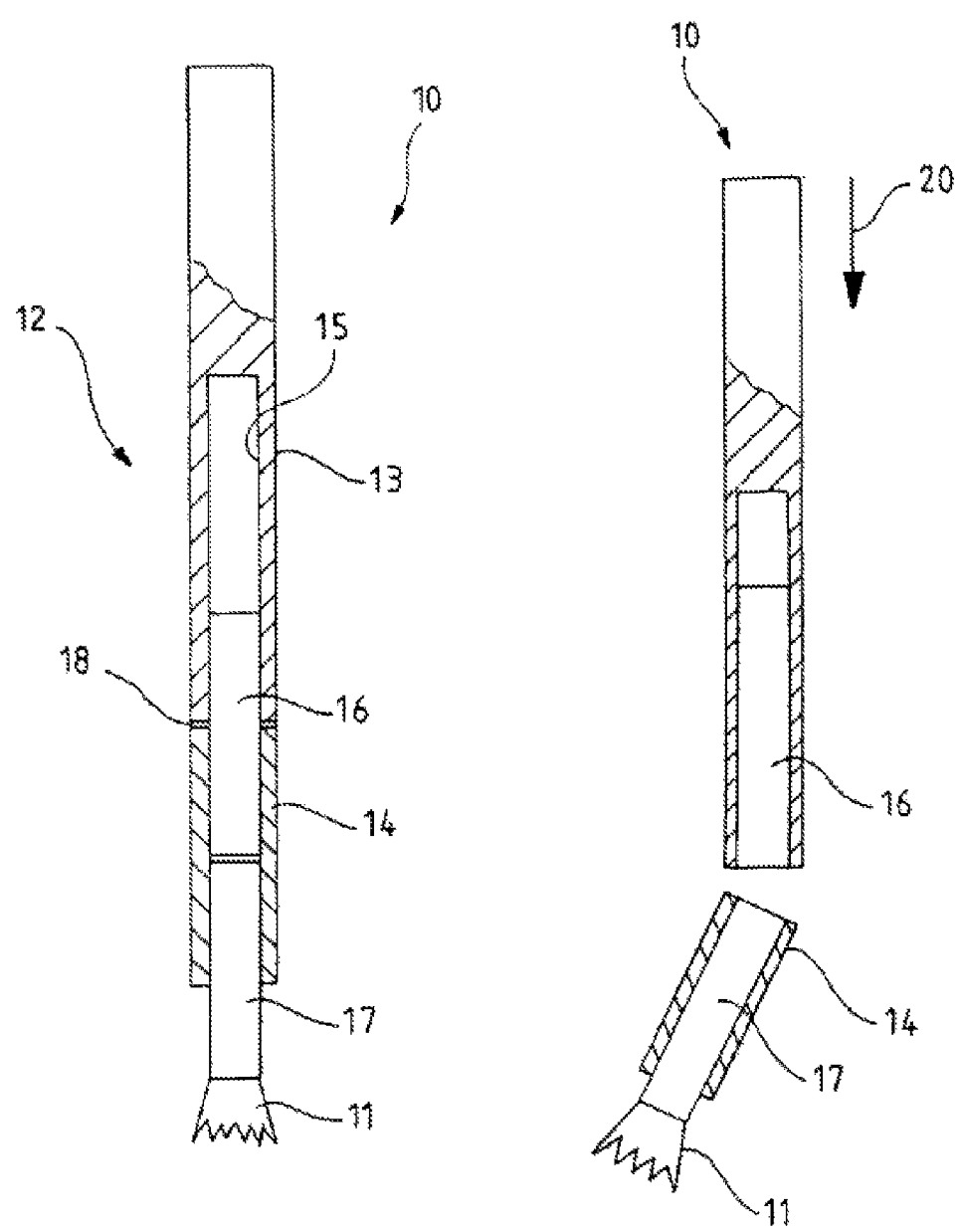
FIG. 1a shows an embodiment example of the device according to the invention according to the first variant in the assembled state, FIG. 1a' shows the same device in the separated state.

FIG. 1a shows a sampling device 10 with a sample-collecting area 11 and a holding device 12. The holding device 12 comprises an upper segment 13 and a sleeve 14 oriented and arranged distally thereto. In the proximal segment, an inner recess 15 is provided, which has substantially the same dimensions as the inner dimensions of the sleeve 14. The connection of the two segments 13 and 14 occurs by means of a plug 16 inserted with little clearance both into the inner recess 15 and also into the sleeve 14. As for the sample-collecting area 11, it is inserted via an extension 17, having generally dimensions corresponding to those of the plug 16, into the distal end region of the sleeve 14. The dimensions of the extension 17, of the plug 16 as well as of the inner recess 15 and of the sleeve 14 are selected so that, in normal operation, a stable connection of all the components to one another is established. In order to ensure that, in the case of incorrect actuation, no undesired separation of the sampling device 10 occurs in the area 18 between the proximal segment 13 and the sleeve 14, a blocking device, which is not shown, can optionally be provided, which limits displacement of the plug 16 in the proximal direction. In this manner, the plug is prevented from being able to be displaced unintentionally over the area 18 into the recess 15.

The blocking device is not necessarily required. In the context of the usual plastic manufacturing processes, it is not a problem to produce the mentioned components of the sampling device with dimensions that are adjusted to one another sufficiently precisely so that, even in normal operation, a reliable connection of all the components by means of the plugs, for example, is ensured, and the risk that said plug is displaced unintentionally into the recess is nearly ruled out. It is also conceivable to secure the components in question by means of positive-lock connections that are easily adjustable to one another with regard to their holding properties, in normal operation.

FIG. 1a' then shows the state of the sampling device 10 with separated sample-collection device 11. For the separation, the proximal end of the proximal segment 13 is exposed to force acting in arrow direction 20, while the distal end of the device, i.e., the sample-collecting area 11, sits in a stationary manner, for example, on the bottom of a laboratory vessel which is not shown. If the proximal segment 13 moves in the direction of the arrow 20, the extension 17 is moved in the proximal direction into the sleeve 14 and displaces the plug 16 after coming in contact completely into the inner recess 15 of the proximal segment 13. When the plug 16 no longer covers the border area 18 between the upper segment 13 and the sleeve 14, the connection is undone in this area, and the sleeve 14 together with the inserted extension 17 and the sample-collecting area 11 automatically separate from the rest of the sampling device 10.

Figure 1B:
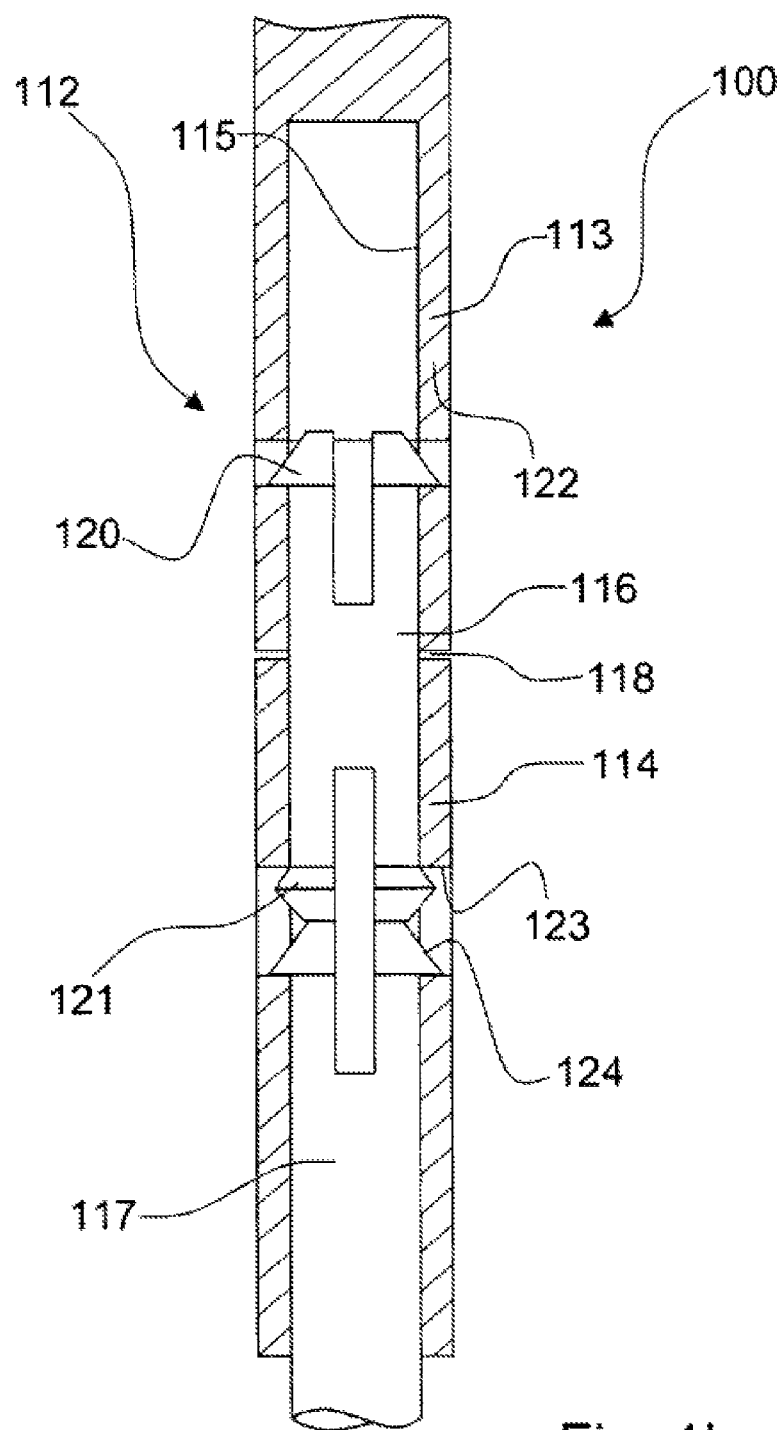
FIG. 1b shows an additional embodiment of the device according to the invention according to the first variant in the assembled state.

FIG. 1b shows a sampling device 100 with a sample collection device held by an extension 117, which is not shown, and a holding device 112. Analogously to FIG. 1a, the holding device 112 also comprises an upper segment 113 and a sleeve 114 oriented distally and arranged flush with respect to said segment.

In the proximal segment, in turn, an inner recess 115 is provided, which has substantially the same dimensions as the inner dimensions of the sleeve 114. The connection of the two segments 113 and 114 occurs with a plug 116 which can be inserted in the two segments.

Unlike FIG. 1a, the plug 116 has on its two ends snap-in noses 120 and 121, each being in snap-in engagement with perforations 122 and 123 provided in the inner recess 113 and the sleeve 114. The proximal end of the extension 117 also has snap-in noses 124 which are in snap-in engagement with the perforation 123.

To release the snap-in engagement, the snap-in noses 120, 121 and 124 can be pressed inward, wherein the snap-in noses are dimensioned so that they allow, in the pressed-in state, a displacement of the extension or of the plug in the sleeve or the inner recess.

All the snap-in noses are provided with bevels, so that they are pressed automatically inward when a pressure acts proximally on the extension, after which extension and plug can be displaced to the point that a separation of the sample-collecting device occurs as shown in FIG. 1a'.

FIGS. 2-6 show additional variants of the sampling device.

Figure 2:
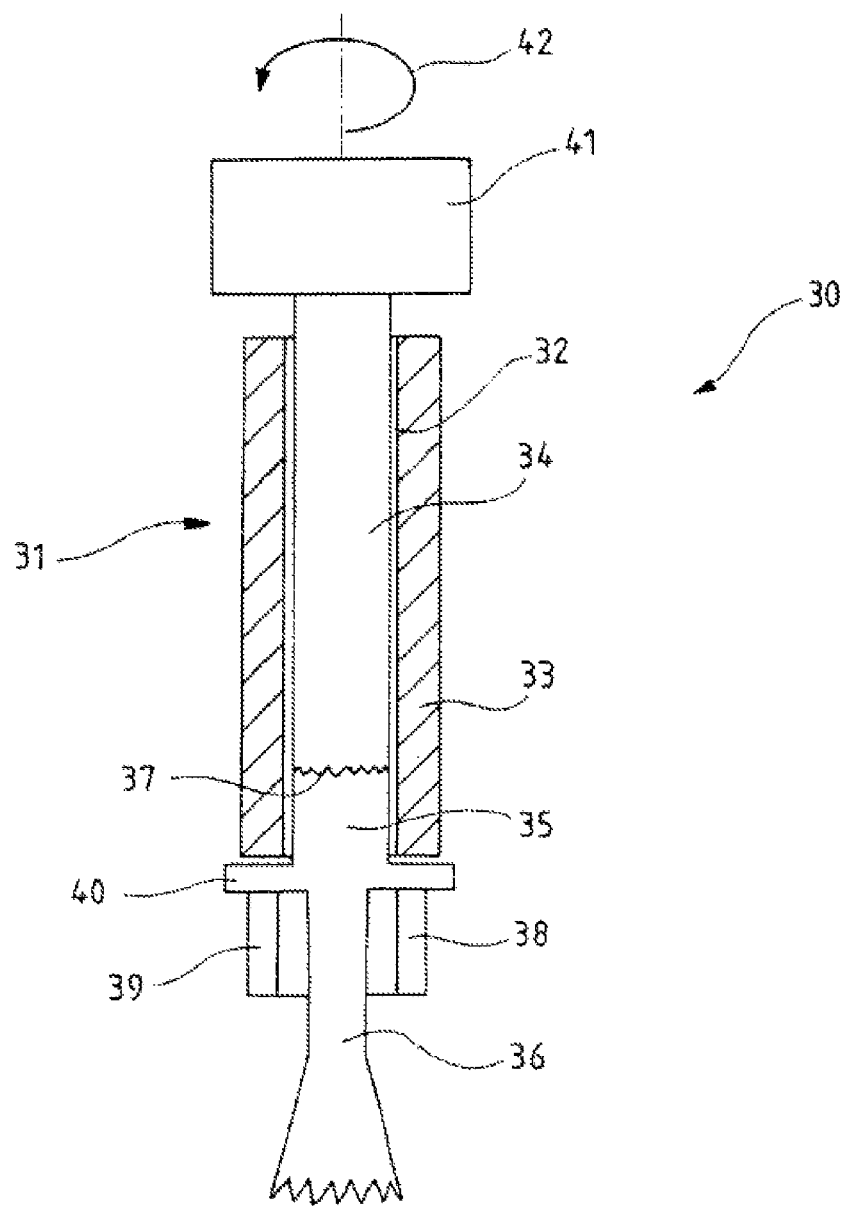
FIG. 2 shows a sampling device according to an additional variant, in which the separation of the sample-collecting area occurs by twisting an internal device relative to an external device of the holding device.

The sampling device 30 shown in FIG. 2 comprises a holding device 31 with an inner rod-shaped device 32 and an external device which encloses the former device and is in the shape of a small tube 33. The inner rod-shaped device comprises a distal segment 34 and a proximal segment 35 on the distal end of which a sample-collecting area 36 is arranged. The proximal segment 34 and the distal segment 35 are connected to one another via a predetermined breaking point 37. At its distal end, the small tube 33 has two slits 38, 39 extending in the longitudinal direction, into which protrusions 40 of the distal segment 35 are inserted. At its proximal end, the proximal segment 34 has an adjustment knob 41 by means of which the rod-shaped internal device 32 can be twisted in the direction of the arrow 42. If during such a twisting the outer small tube 33 is immobilized, then the proximal segment 34 of the rod-shaped device 32 is twisted at the predetermined breaking point 37 off of the distal segment that is secured in a torque-proof manner in the slits 38, 39, and this segment with the sample-collecting area 36 attached thereto can then fall downward out of the holding device 31.

In FIG. 3, the sampling device 50 is shown, which again has a holding device 51 for a distal sample-collecting area 52 with an inner rod-shaped device 53 and a tube-shaped external device 54 enclosing said inner rod-shaped device. The rod-shaped device 53 again has a proximal segment 55 which projects upward out of the small tube 54 and a distal segment 56 which carries the sample-collecting area 52. There is no connection between distal segment 56 and the proximal segment 55, i.e., the two parts aligning flush in the sleeve-shaped external device 54.

The rod-shaped device 52 is secured by means of a cap 57 against undesired displacement during the sampling. The distal segment 56 moreover is secured against falling out, etc., by means of a positive-lock engagement 58 in the small tube 54.

If the sample-collecting area 52 then needs to be separated, the cap 57 is then removed and the rod-shaped device 55 is pressed sufficiently far into the sleeve 54, until the distal segment 56 is pushed forward completely downward and can fall out of the sleeve 54. Naturally, it is also conceivable for the sleeve 54 to be moved upward relative to the small rod, as a result of which the same effect then occurs.

FIG. 4 shows an embodiment in which a soft cap 57' is provided, which encloses the proximally projecting end of the small-rod-shaped device 55. The cap 57' is made of a soft material and it allows an actuation similar to that of a ballpoint pen.

Figure 5B:
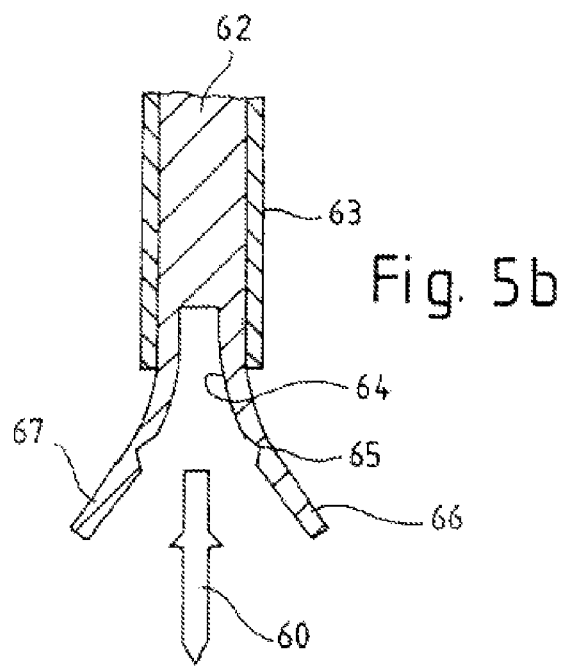

FIGS. 5a and 5b show alternatives for the accommodation of a distal segment 60 in a holding device 61. In this case, an inner small-rod-shaped device 62 is provided, which is enclosed by a small tube 63. At its distal end, in the small-rod-shaped device 62, a slit 64 extending in the longitudinal direction is provided, in which the distal segment 60 is arranged with positive-lock engagement 65. If now, as shown in FIG. 5b, the inner small-rod-shaped segment 62 is pushed downward out of the small tube 63, then the segments 66 and 67 of the inner rod-shaped device, which delimit the slit 64, are flipped outward and they release the positive-lock connection to the distal segment 60.

Finally, an additional variant provides a holding device 70 which again has an internal device 71, in particular in the form of an inner small rod, and an external device 72 oriented parallel thereto and at least partially enclosing the small rod. External device 72 and rods 71 are inserted at their distal end with a tight fit into a recess 73 which carries, at its other end, a sample-collecting area 74. If now, as a result of a relative movement between internal and external devices, the external device 72 is pulled out of the recess 73, then the connection between holding device and recess is undone, and the recess is automatically separated with the sample-collecting area attached thereto.

The invention claimed is:

1. A sampling device for samples containing DNA comprising an elongate holding device and a sample collecting area provided at a free end of the elongate holding device wherein the sample-collecting area is separable from the sampling device, wherein the holding device when viewed in a longitudinal direction, has a proximal segment with an inner recess extending from a distal end thereof at least over a longitudinal area in a proximal direction, and a distal sleeve that is aligned flush with respect to the recess wherein the proximal segment and the distal sleeve are connected to one another by means of a plug that is inserted with little clearance in the inner recess and the sleeve wherein the dimensions of the plug of the sleeve and of the inner recess are adjusted to one another such that in normal operation a stable connection of the proximal segment to the sleeve is established, and wherein the sample-collecting area is arranged on an elongate extension whose free end is inserted in turn with little clearance in a distal end of the sleeve wherein lengths of the inner recess, of the sleeve of the plug and of the extension are adjusted to one another such that the plug can be completely inserted into the recess in the case of a proximally directed displacement of the extension relative to the sleeve.

2. The sampling device according to claim 1, wherein the dimensions of the inner recess of the sleeve of the plug and of the extension are adjusted to one another so that plug and/or extension are received with a tight fit in the sleeve and/or in the inner recess.

3. The sampling device according to claim 1, wherein the plug and/or extension is/are secured in the sleeve and/or inner recess by means of a positive-fit connection.

4. The sampling device according to claim 3, wherein the positive-fit connection is a snap-in connection.

5. The sampling device according to claim 1, wherein a blocking element that limits relative displacement of the plug in the inner recess is provided.

6. A sampling device for samples containing DNA comprising an elongate holding device and a sample collecting area provided at a free end of the elongate holding device wherein the sample-collecting area is separable from the sampling device, wherein the holding device comprises an inner rod-shaped device on a distal end of which the sample-collecting area is arranged, and an external device that encloses the inner rod-shaped device at least partially and wherein distal ends of the internal rod-shaped device and of the external device of the holding device are inserted with a tight fit in a recess which supports the sample-collecting area at its other end, wherein the internal rod-shaped and external devices are formed so that they can be displaced in a longitudinal direction relative to one another, and a connection between holding device and recess can be separated by a corresponding relative movement.

7. The sampling device according to claim 6, wherein the internal rod-shaped device has a proximal segment and a distal segment connected thereto via a predetermined breaking point wherein the distal segment supports the sample-collecting area-wherein the external device is in the form of a small tube which partially encloses the internal rod-shaped device wherein the distal segment is received in the tube so that it can be displaced in a longitudinal direction and the internal rod-shaped device is secured against torsion.

8. The sampling device according to claim 6, wherein the internal rod-shaped device has a distal segment supporting the sample-collecting area and a proximal segment arranged so that it adjoins said distal segment but is not connected thereto.

* * * * *